United States Patent [19]

Rajagopal et al.

[11] Patent Number: 5,610,325
[45] Date of Patent: Mar. 11, 1997

[54] TORSIONAL RHEOMETER FOR GRANULAR MATERIALS SLURRIES AND GAS-SOLID MIXTURES AND RELATED METHODS

[75] Inventors: Chandrika Rajagopal; Kumbakonam R. Rajagopal; Rattaya C. Yalamanchili, all of Allison Park, Pa.

[73] Assignee: Viscoustech, Inc., Pittsburgh, Pa.

[21] Appl. No.: 464,325

[22] Filed: Jun. 5, 1995

[51] Int. Cl.⁶ .................................................. G01N 11/14
[52] U.S. Cl. .................... 73/54.39; 73/54.38; 73/54.35
[58] Field of Search ................................ 73/54.28, 54.31, 73/54.32, 54.33, 54.34, 54.35, 54.37, 54.38, 54.39, 846

[56] References Cited

U.S. PATENT DOCUMENTS

| | | | |
|---|---|---|---|
| 2,752,778 | 7/1956 | Roberts et al. | 73/54.32 |
| 3,535,914 | 10/1970 | Veith et al. | 73/54.39 X |
| 4,173,142 | 11/1979 | Heinz | 73/54.32 |
| 4,343,190 | 8/1982 | Danko et al. | 73/54.39 X |
| 4,601,195 | 7/1986 | Garritano | 73/54.39 X |
| 5,103,679 | 4/1992 | Porter et al. | 73/54.39 X |
| 5,167,143 | 12/1992 | Brookfield | 73/54.23 |
| 5,209,108 | 5/1993 | Shackelford | 73/54.28 |
| 5,269,190 | 12/1993 | Kramer et al. | 73/822 |
| 5,271,266 | 12/1993 | Eschbach | 73/54.33 |
| 5,277,058 | 1/1994 | Kalyon et al. | 73/54.11 |
| 5,302,878 | 4/1994 | Sourcemarianadin et al. | 310/360 |
| 5,303,578 | 4/1994 | Williams et al. | 73/54.24 |
| 5,315,863 | 5/1994 | Cowper | 73/54.09 |
| 5,347,852 | 9/1994 | Mode | 73/54.04 |
| 5,349,847 | 9/1994 | Lee et al. | 73/54.33 |
| 5,357,783 | 10/1994 | Eschbach | 73/54.23 |

OTHER PUBLICATIONS

Van Wazer et al., "Viscosity and Flow Measurement", Interscience publishers, pp. 72–75, 87–95, 113–116, QC 189V3 1963.

*Primary Examiner*—Michael Brock
*Attorney, Agent, or Firm*—Arnold B. Silverman; Eckert Seamans Cherin & Mellott

[57] ABSTRACT

A torsional rheometer apparatus for determining rheological properties of a specimen is provided. A stationary plate and a rotatable plate are in generally coaxial position and structured to receive a specimen therebetween. In one embodiment, at least one of the plates and preferably both have roughened specimen engaging surfaces to serve to reduce undesired slippage between the plate and the specimen. A motor is provided to rotate the rotatable plate and a transducer for monitoring forces applied to the stationary plate and generating output signals to a computer which determines the desired rheological properties are provided. In one embodiment, the roughened surfaces consist of projections extending toward the specimen. Where granular material is being evaluated, it is preferred that the roughness of the plate is generally equal to the average size of the granular material being processed. In another embodiment, an air-solid mixture is processed and the roughened portions are pore openings in the plates. Air flows through the region between the two pore containing plates to maintain the solid materials in suspension. In yet another embodiment, the base of the stationary plate is provided with a deformable capacitance sensor and associated electronic means.

34 Claims, 7 Drawing Sheets

TORSIONAL RHEOMETER FOR GRANULAR MATERIALS SLURRIES AND GAS-SOLID MIXTURES AND RELATED METHODS

GOVERNMENT RIGHTS

This invention was made with Government support under Contract No. DE-FG02-92ER 81429 awarded by the Department of Energy. The Government has certain rights in this invention.

BACKGROUND OF THE INVENTION

1. Field of the Invention

The present invention provides a system for rheologically evaluating a wide rage of materials ad, more specifically, it provides such a system which has positive means for effecting more efficient measurement of the rheological properties of the specimen.

2. Description of the Prior Art

It has long been own that various properties of certain materials can be measured effectively using rheometers.

U.S. Pat. No. 5,209,108 discloses a axial rheometer wherein a computer processes signs receive from pressure sensing means and speed sensing means.

U.S. Pat. No. 5,269,190 discloses an axial rheometer wherein a microprocessor causes axial displacement of the sample holder to deform the sample.

U.S. Pat. No. 5,277,058 discloses an adjustable gap rheometer wherein the dimension between a stationary section and a movable section is altered to facilite determination of shear rate and shear stress for varying deformation rates.

U.S. Pat. No. 5,315,863 discloses measurement of a fluid or a slurry in a continuous on-line measurement determined rheological properties. An inverted U-tube is employed with pressures being compared at a point in each leg. U.S. Pat. No. 5,347,852 also discloses an on-line rheological measurement apparatus wherein a portion of the melt is diverted to a capillary passage by means of a first metering pump and is returned by means of a second metering pump.

It has been known to measure dynamic shear properties employing a rheometer wherein a stationary plate and a rotatable plate are provided with a specimen therebetween. The rotatable plate is subject to oscillating movement relative to the stationary plate. This system measures torque during a predetermined angular rotation and employs a transducer and computer to calculate the rheological properties at different temperatures. See U.S. Pat. No. 5,357,783 and also the two surface oscillating plate of related U.S. Pat. No. 5,271,265.

U.S. Pat. No. 5,303,578 also discloses a dynamic rheometer. This patent discloses shear waves impinging on two spaced shear receiving surfaces with a transducer being provided for each surface.

U.S. Pat. No. 5,302,878 discloses a high-feed acoustic rheometer wherein a torsional-mode transducer in a cylinder interacts with a sensor in a rod with the respective diameters of the torsional-mode transducer and the sensor being such that the coefficient of reflection at the interface of the transducer-sensor is zero.

U.S. Pat. No. 5,167,143 discloses a rheometer having a motor driven chamber which is said to be usable for measuring fluids, slurries and finely divided particulated solids. An annular gap is provided between the motor driven chamber and spindle with an associated transducer being employed. The system is said to convert shear into viscosity.

U.S. Pat. No. 5,349,847 discloses a rotatable rheometer wherein the rotatable plate, specimen and stationary plate are adapted to be separated from the thick support which supports the stationary plate with magnetic means employed to effect retention. This is said to facilitate more efficient operation of the equipment which can be switched from operation in a rotational mode to operation in an oscillating mode.

In spite of this known system, there remains a very real and substantial need for an improved type of rotary rheometer which will effect more efficient interengagement between the specimen and the plates in order to provide more accurate results.

SUMMARY OF THE INVENTION

The present invention has met the hereinbefore described needs. The present invention provides a torsional rheometer and associated method for determining rheological properties of a specimen with the system operating either in a pure rotational mode or in an oscillatory mode. In the pure rotational mode, the shear properties of the material are determined in a steady state manner. In the oscillating mode, intrinsic properties are determined during oscillation over a predetermined arc.

The apparatus includes a stationary plate and a generally coaxial rotatable plate which are structured to receive a specimen therebetween. At least one and, in the preferred embodiment, both of the plates have the surface facing the specimen roughened in order to provide for more efficient interengagement with the specimen to resist undesired slippage of the specimen. Motor means are provided for effecting rotation or oscillation of the rotatable plate which is preferably positioned in overlying relationship with respect to the stationary plate. Transducer means monitor forces applied to the stationary plate during rotation of the rotatable plate and emit responsive signals to computer means which may be a microprocessor, miniprocessor, personal computer, or main frame computer. The computer means employs the transducer signals to determine the desired rheological properties.

Control means are provided for determining whether the rotary motion will be repeated rotary motion over a 360° arc or will be oscillating motion within a predetermined angle of oscillation. The degree of roughness of the roughened surface is preferably related to the nature of the material which will be subjected to rheological evaluation. The associated method provides for producing specimens between the rotatable plate and stationary plate and effecting either 360° repeated rotation or oscillating rotation such that the forces applied to the stationary plate during motion can be converted by a transducer into a corresponding electrical output signals which a processor receives and converts into the desired rheological properties.

It is an object of the present invention to provide rotary rheological apparatus and an associated method which will provide more efficient interengagement between the specimen contacting plates and the specimen.

It is another object of the present invention to provide such a system wherein a wide variety of materials, including granular materials, slurries, highly viscoelastic materials and gas-solid mixtures may be evaluated rheologically.

It is a further object of the present invention to provide such a system which is compatible with existing equipment and may provide the benefits thereof without requiting major changes in apparatus or methods.

It is a further object of the present invention to provide such a system which can test gas-solid mixtures as a mixture as distinguished from as individual components.

In another embodiment of the invention, a stationary plate having a base formed as a capacitor may be provided.

These and other objects of the invention will be more fully understood from the following detailed description of the invention on reference to the illustrations appended hereto.

DESCRIPTION OF THE PREFERRED EMBODIMENTS

As employed herein, the term "roughened surface" will refer to a surface of either a rotatable plate or stationary plate which is adapted to contact a specimen to be rheologically examined with the surface being discontinuous either due to (a) outwardly projecting elements of the plate material, or (b) pores which pass through the entire plate.

Figure 1:
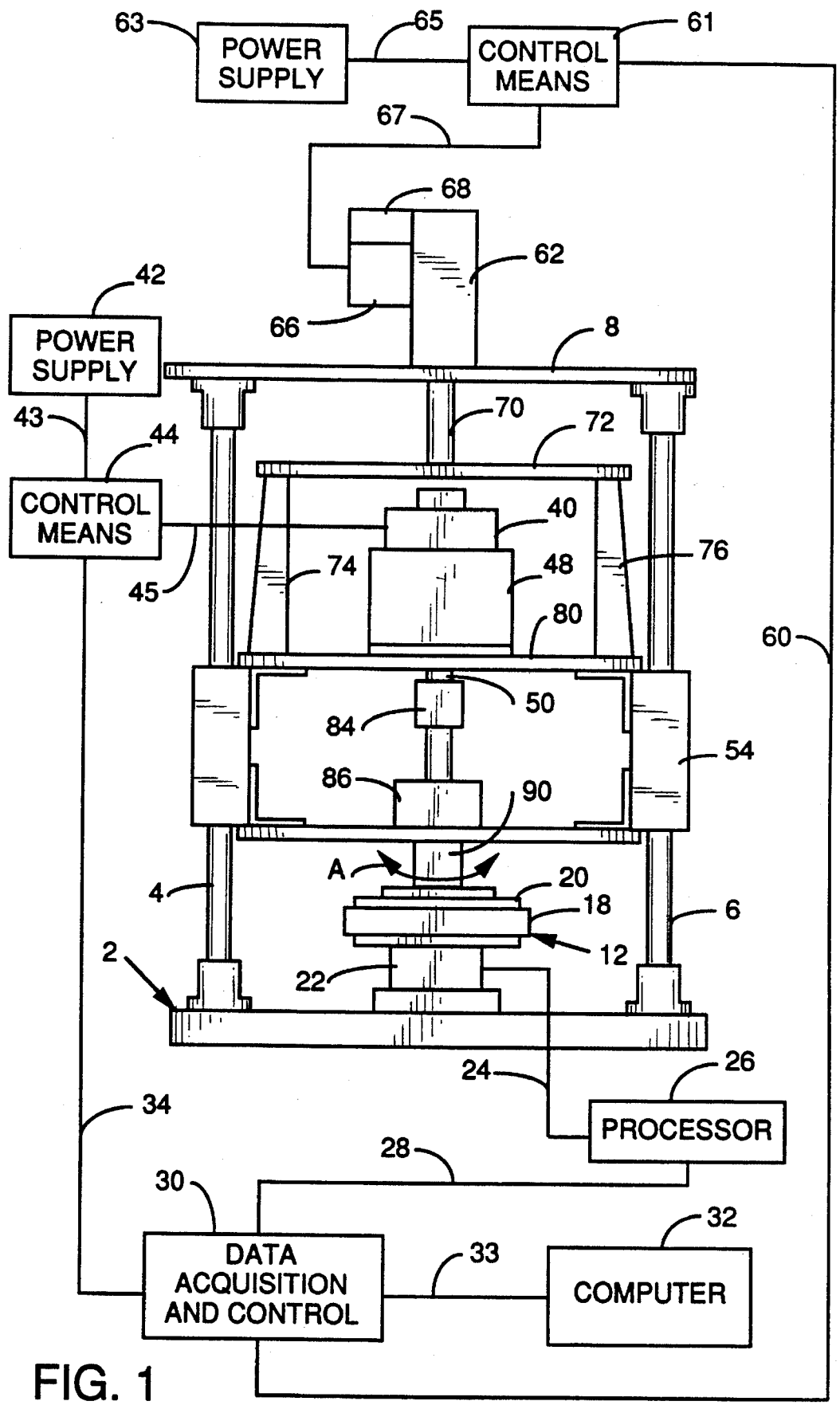
FIG. 1 is a partially schematic elevational view of a form of apparatus of the present invention.

The apparatus shown in FIG. 1 may have a conventional support frame consisting of a pedestal 2 with four vertical posts 4, 6 and two spaced behind plates 4 and 6 (not shown), which may be of the same shape as those shown, supporting an upper platform 8. The upper and lower plate system 12 which will be discussed hereinafter as a stationary plate 18 which receives a rotatable plate 20. Transducer 22 underlies and is operatively associated with stationary plate 18 such that when axial rotation is effected in one of the directions indicated by arrow A, either in repeated 360° degree cycles of rotation in the same direction, or in an oscillating movement, the stresses will result in the stationary plate 18 receiving through the specimen forces which may be projected in three orthogonal directions and torque. This series of forces applied to transducer 22 will result in a plurality of output signals over lead 24 to processor 26 which may be any sort of computer means. The processor 26 converts the output of transducer 22 which is the nature of a charge to a voltage and emits an output signal over lead 28 to data acquisition and control unit 30 which delivers the signals to computer means 32 for processing and storage over lead 33. The computer means 32 will determine the rheological properties viscosity of the material. Such properties may be viscosity and stresses in a direction normal to the rotatable plate 20. These properties may be stored, computer enhanced, displayed or made the subject of hard copy as desired. Among the suitable transducers, usable as transducer 22, is a piezoelectric four component transducer available from Kistler Instrument Corporation. Suitable software for use in the computer means 32 is that sold by National Instruments under the trade designation Lab VIEW. The wide range capability in respect of loads on the transducer 22 facilitates use of the system of the present invention with a wide range from granular materials, such as coal and rice, for example, to thick sludge similar to bread making dough, for example.

The transducer 22 will generally provide output signals which are responsive to the torque and axial force. If a coordinate system has the x and y axes in the plane of shear, which is generally parallel to the plates 18, 20, with the z axis directed upwardly, the transducer will provide a reading of (a) the axial force along the z axis, i.e., normal to the shear plane and (b) two forces that are perpendicular to one another in the plane of shear. The torque represents a moment about the z axis. When the rotatable plate 20 and the stationary plate 18 are coaxial the two forces normal to each other in the plane of shear during axial 360° rotation or oscillation will generally be zero, i.e., when the rheometer is in a torsional configuration. The forces monitored to determine rheological properties are, therefore, the normal or z axis force and the moment force which represents torque.

A motor 40, which is energized over lead 45 by a suitable power supply 42 through lead 43 to control means 44 is shown overlying the plate assembly 12. The motor is adapted to effect rotary movement of rotatable plate 20. It will be appreciated that the control means 44 receives control signals from computer means 32 through a data acquisition and control unit 30 over lead 34. This facilitates electrical switching to effect operation of the motor 40 in a first mode which provides continuous 360° axial rotation of rotatable plate 20 and in a second mode which provides for angular oscillation of rotatable plate 20 through a desired arc which may be on the order of +90° to −90° at 15 Hz, +35° to −35° at 25 Hz and +9° to −9° at 50 Hz, for example. The output of the motor 40 is converted to the desired speed through an appropriate gear box 48 and delivers rotary motion to output shaft 50. In order to facilitate relative separating movement between stationary plate 18 and rotary plate 20, the plate 20 is adapted to be translated axially moving with an assembly that rides on liner bearings 54. Once the specimen is in place, axial movement of the plate 20 in the reverse direction, i.e., toward the stationary plate 18 is also effected to effect initial compaction of the specimen. Control of operation of this function is effected by computer means 32 by its LabVIEW software by emitting appropriate signals through acquisition and control unit 30 over lead 60 to control means 61 which may be a three-axis controller of the type available from NuLogic. Power supply 63 has output over lead 65 enter control means which emits a signal over lead 67 to servo motor 66 and through a gear box 68 to ball screw and nut 62 which moves shaft 70 vertically in an up and down path. Shaft 70 is fixedly secured to upper support 72 which has four depending supports with 74 and 76 being shown, secured to lower support 80 which, in turn, is secured to the liner bearings 54. The motor shaft 50 is coupled to plate shaft 90 using a low or no backlash coupler 84. The vertical orientation of the plate shaft 90 is achieved with assistance of bearing assembly 86 which, in the form shown, has two tapered roller bearings. The rotatable upper plate 20 is mounted on shaft 90 and may easily be changed, if desired, for the particular specimen being tested.

Figure 2:
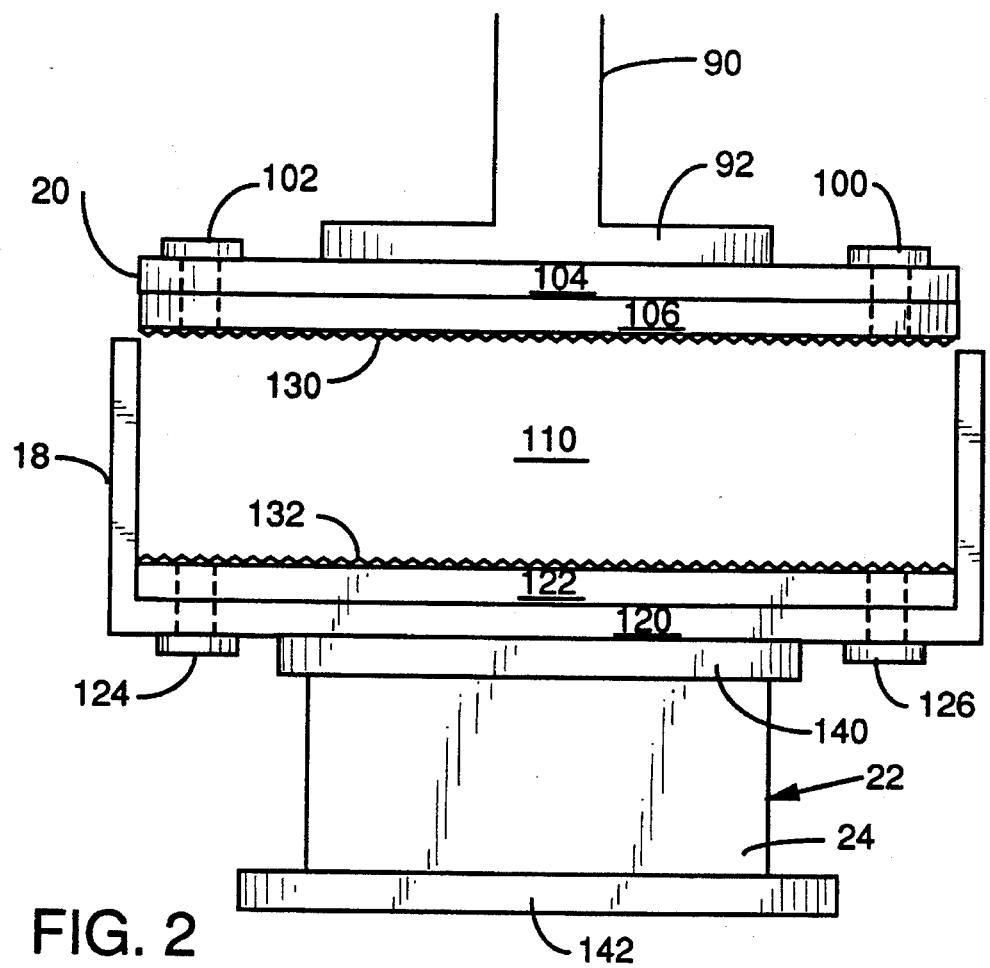
FIG. 2 is a fragmentary elevational view showing the rotatable and stationary plates of the present invention in relative open position.

Referring to FIG. 2, there is shown a more detailed view of rotary plate 20 and stationary plate 18, as well as transducer 22. It will be noted that the rotatable plate 20 is fixedly secured to annular flange 92 of shaft 90 with bolts 100, 102 securing an upper portion 104 of the rotatable plate to a lower portion 106 of the rotatable plate. The stationary plate 18 has an upwardly projecting annular wall and is generally cup-shaped. Plate 18 defines an upwardly open chamber 110 which is of greater diameter than rotatable plate 20 so that the rotatable plate can be received within chamber 110. The lower plate has two elements 120, 122 with a pair of bolts 124, 126 securing the assembly. In essence, this approach provides means for replacing plate elements 106 and 122, which are generally circular, after wear or in the event of damage. An important aspect of the present invention is that the lower surface 130 of plate element 106, which is the portion of the plate which faces the specimen which will be received in chamber 110, is roughened. The degree of roughening may be varied depending on the material being analyzed. Similarly, surface 132 of stationary plate portion 122 has its surface, which will face and contact the specimen, roughened. It will be appreciated that the transducer 22 has an annular plate 140 fixedly secured to the upper end thereof which, in turn, is secured to the lower surface of stationary plate 18 such that forces applied to the stationary plate 18 will be transferred to the transducer 22 to facilitate an electrical output signal over lead 24 to processor 26. A pedestal supporting base 142 is secured to the lower surface of transducer 22.

Figure 3:
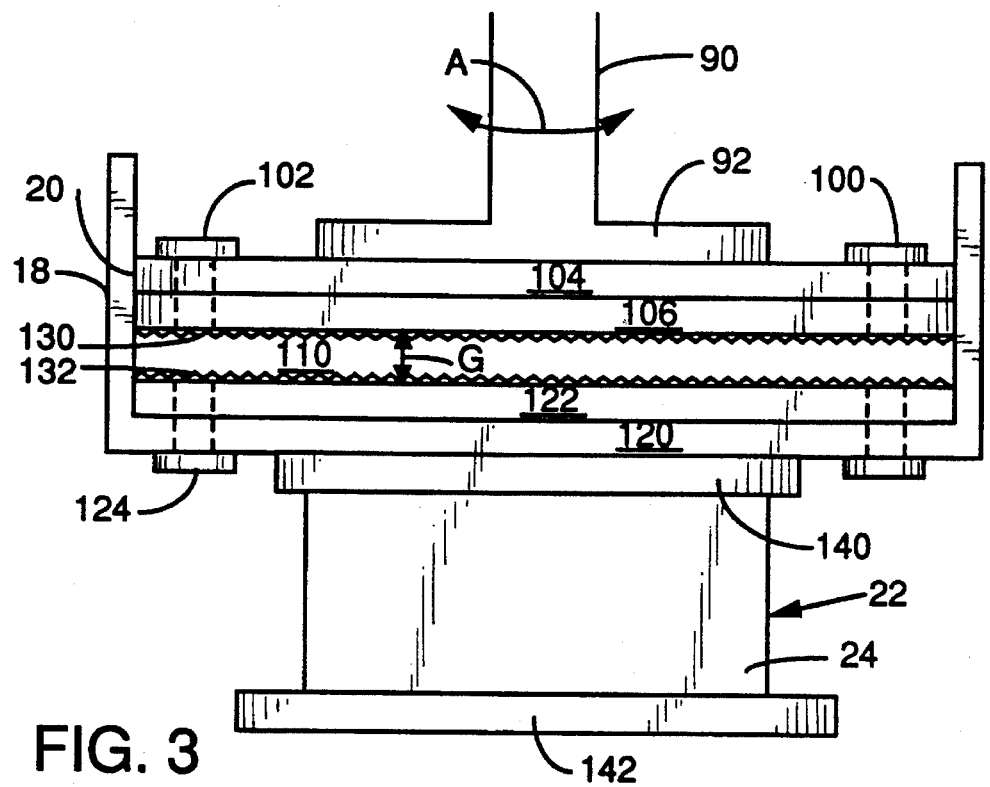
FIG. 3 is a view similar to FIG. 2, but showing the plates in relative closed position.

FIG. 3 is similar to FIG. 2, except shows the plates 20, 18 in relative closed position such that chamber 110 is relatively small. A specimen would normally be placed into the chamber with the roughened surfaces 130, 132 being in intimate contact therewith and penetrating the same to provide firm interengagement. The specimen, which would fill chamber 110, has not been shown for clarity of illustration.

Figure 4A:
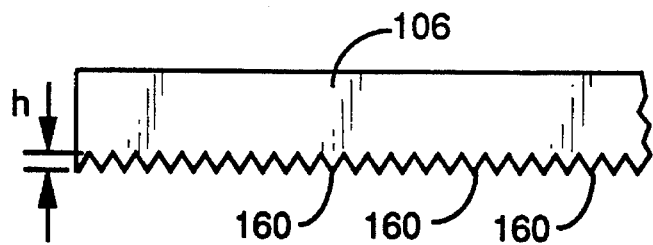
FIG. 4A is a schematic illustration showing a portion of the rotatable plate with the roughened portions integrally formed.
Figure 4B:
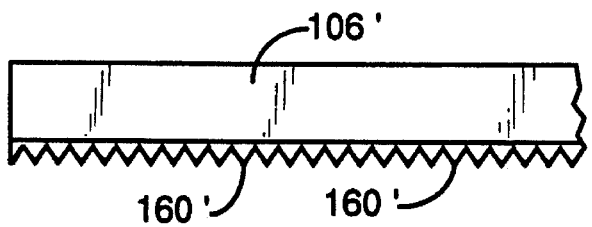
FIG. 4B is similar to 4A, but shows the roughened portions applied as a coating.

Referring now to FIG. 4A, there is shown by way of an example, a part of lower portion 106 of the rotatable plate wherein a plurality of integrally formed projections 160, which preferably cover the entire surface of lower portion 106. The projections 160 have a height "h" which may generally be in the range of about 10 microns to 1 cm. The projections 160 preferably will have a shape which has alternating peaks and grooves. The size and shape may vary, as to granular materials, to correspond generally to the size and shape of the granular materials and will be uniformly spaced from each other such that the entire roughened surface will have projections of generally uniform shape and dimension with the identical relative spacing. It will be appreciated that the roughened surface 132 (FIG. 3) of stationary plate element 122 may have substantially identical configuration as plate element 106. The plates may preferably be made of steel, stainless steel, cast iron, copper, brass, aluminum, resinous plastic or plexiglas with the roughened projections 160 being integrally formed therein. An alternate embodiment is shown in FIG. 4B wherein the plate element 106 has a plurality of similarly configured projections 160' provided by a coating which may consist of abrasive containing materials, or materials such as sand, coal, powder, grain or other suitable materials glued or otherwise fixed to the surface of the plate.

Figure 4C:
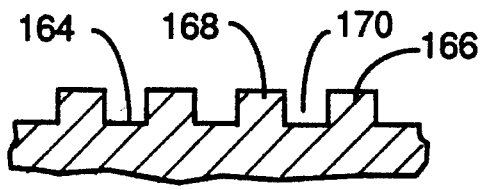
FIG. 4C through 4G show cross-sectional examples of shapes and spacing of projections usable in the roughened surfaces of the present invention.
Figure 4D:
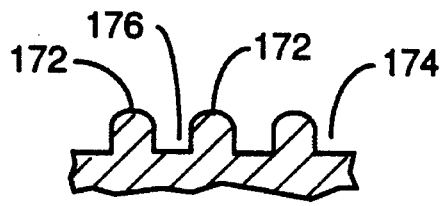

FIG. 4C shows a portion of a roughened surface of the present invention wherein the surface 164 cooperates with a plurality of generally rectangular projections 166, 168 having a rectangular shape in plan and defining a plurality of grooves 170 therebetween. FIG. 4D has a plurality of projections 172 cooperating with surface 174 to define a plurality of grooves, such as 176.

Figure 4E:
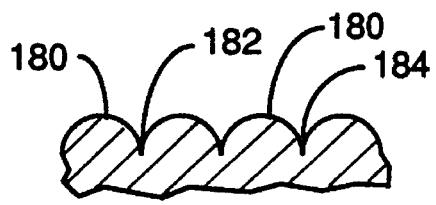
Figure 4F:
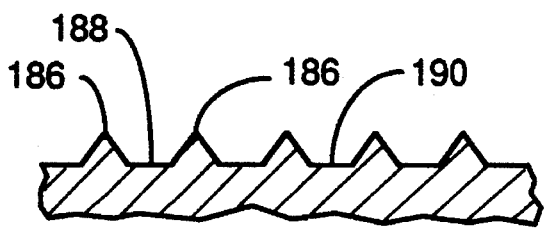
Figure 4G:
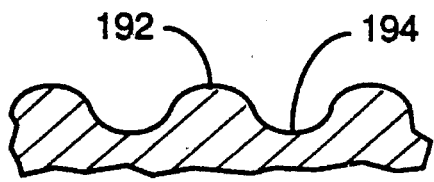

FIG. 4E has a plurality of projections 180 having curved sidewalls 182 defining grooves 184. FIG. 4F has a plurality of projections 186 generally similar to those of FIG. 4A, but having a larger base 188 between projections 186. Grooves 190 which, in the form shown, are generally U-shaped may be of any desired shape. FIG. 4G has a plurality of projections 192 with grooves 194 therebetween.

It will be appreciated from FIGS. 4A through 4G that various projection shapes, sizes and relative spacing provided are examples of different size grooves and different roughened surfaces. These roughened surfaces, if desired, may be provided by coatings or be integrally formed.

When granular material is subjected to rheological analysis by the system of the present invention, it is preferred that the average size and shape of the granules approximate the height and shape of the projections 160. In the case of a slurry, thick sludge, bread making dough, or the like, the surface projections will preferably be large enough so that slipping between the test material and the sample does not occur. In general, these projections are in the shape shown in FIG. 4A with the depth of the projection being about 5 mm to 10 mm depending upon the consistency of the sample. Even in test materials, such as light grease, which adhere to the surface of the plate, the plate surfaces need to be roughened to resist stick slip. While initially there might be no slipping, once the rotatable plate moves above a certain shear rate, the material starts to slip without use of the projections.

Figure 5:
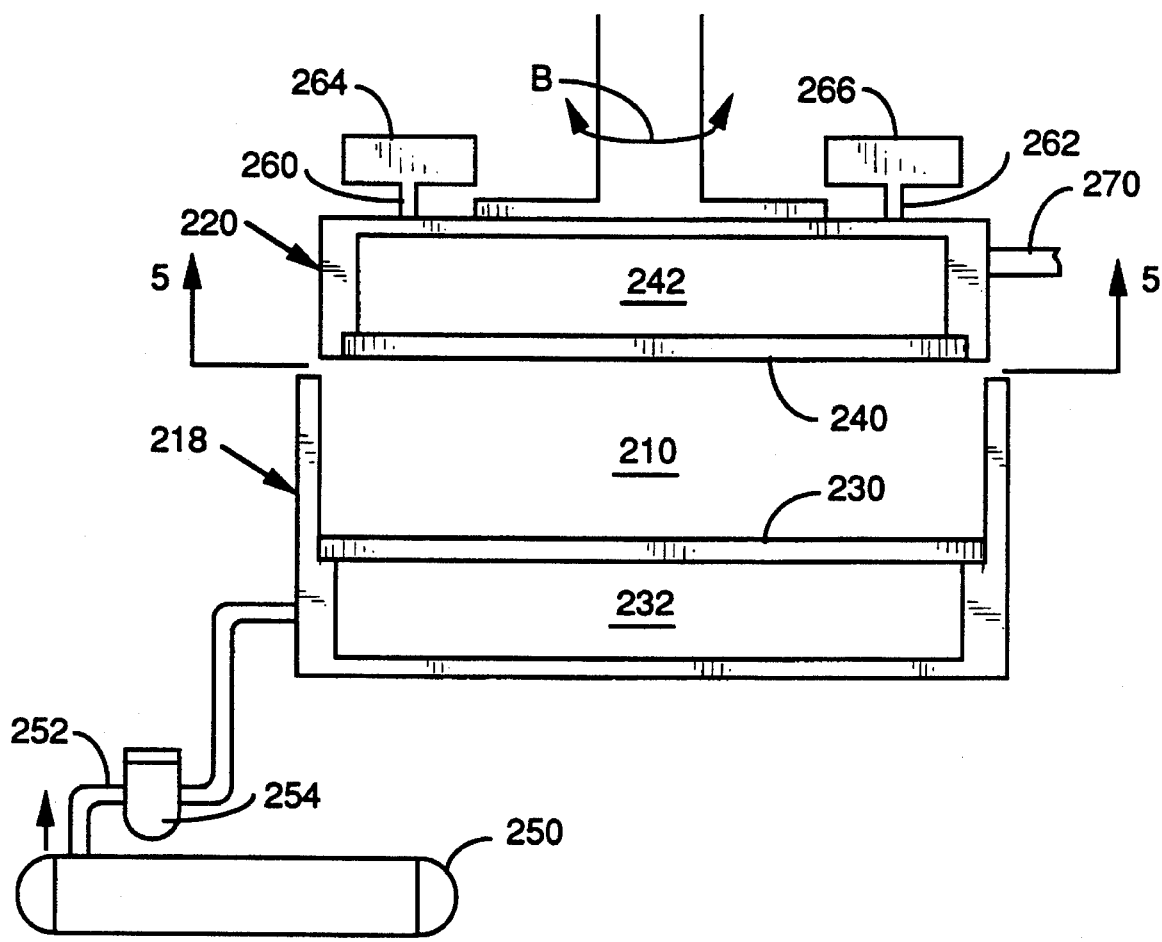
FIG. 5 is a fragmentary cross-sectional illustration showing apparatus similar to FIG. 1, but with some features uniquely designed to make it employable with air-solid mixtures.
Figure 6:
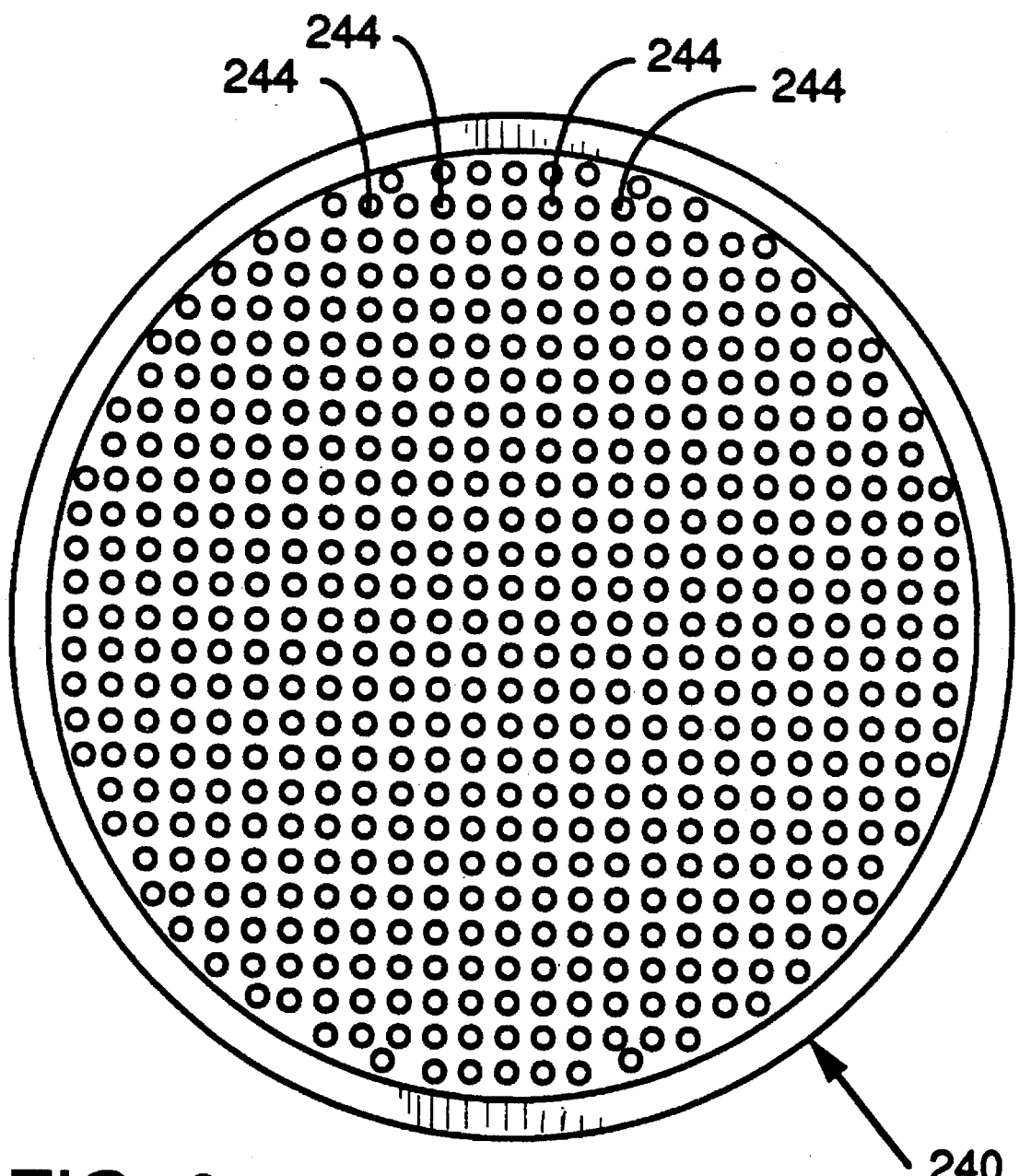
FIG. 6 is a plan view of a form of porous plate usable in FIG. 5.

Referring to FIGS. 5 and 6, a further embodiment of the present invention will be considered. This embodiment is adapted for use with gas-solid mixtures. While it has been known to attempt to do studies on gas having entrained solids, there has not been an effective means of rheologically evaluating the mixture of both. In this embodiment of the invention, the lower plate 218 is generally cup-shaped and provides an upwardly open chamber 210 which receives the specimen. The rotatable upper plate 220 is not only mounted for axial rotation as indicated by arrow B, either through repeated 360° cycles or by oscillation through an arc, which may be on the order of +90° to −90° at 15 Hz, +35° to −35° at 25 Hz, and +9° to −9° at 50 Hz, but also may be subjected to axial movement to separate plates 218, 220 to facilitate sample insertion and relative closing movement to permit plate 220 to enter cavity 210 to provide the desired specimen receiving volume between the circular plates 218, 220. It will be noted that underlying stationary plate element 230 is a chamber 232 which is adapted to receive air. Similarly, overlying plate element 240 is a chamber 242 which is adapted to receive air. As is shown in FIG. 6, upper plate 240 has a plurality of pores 244 which will cover essentially the entire plate with all of the pores 244 being essentially the same size and generally equally spaced from each other. The pore sizes of both plates 230, 240 and spacings are preferably identical for most specimens. The pore openings 244 should be such that they are smaller than the average size of the solid particulate material entrained in the gas to resist clogging of the pores by the solid particles. In the event the process is employed to determine rheological properties of fine powders, the plates may be made of sintered material of various pore sizes to obtain micro-pores.

The mechanics of performing the rheological testing may be essentially as that described with respect to FIG. 1 with certain supplemental apparatus and practices being employed. A compressor 250 provides air through tube 252 and air filter 254 which is adapted to remove material entrained within the air. Tube 252 is in communication with chamber 232 and introduces air into the chamber which air passes upwardly through the pores in plate 230 to impinge upon the sample which is a mixture of gas and solids and maintain the solids distributed within the gas. (If the solids in the specimen are mixed with a gas other than air, it may be desirable to provide an airtight chamber around the plates 218, 220 and employ circulating gas in lieu of air in order to resist contamination of the gas by air.) The air then flows out of chamber 210 through pores in plate 240 into chamber 242. The air in chamber 242 is exhausted through tubes 260, 262 and, respectively, air filters 264,266 so as to remove any undesired entrained particles. When the apparatus is not in operation, nozzle 270 may be employed to pump air into chamber 242 to clear any clogged pores that may be in the plate in plate 240 after the experiment.

It will be apparent that, if desired, the plates 230, 240 may be substituted for by plates having different porosity for particular types of samples or experimental needs.

By providing for more effective interengagement relatively slip-free interaction between the rotary plate and the stationary plate, on the one hand, and the specimen, more accurate results regarding the rheological properties of the specimen, such as viscosity, may be obtained. Normal stress differences may be determined based on the mathematical model to be employed to describe the behavior of the specimen being tested.

The integrally formed roughened surfaces of the present invention may be created by any desired means, such as milling machines, electrochemical machines or for very small projections, chemical etching techniques.

Figure 7:
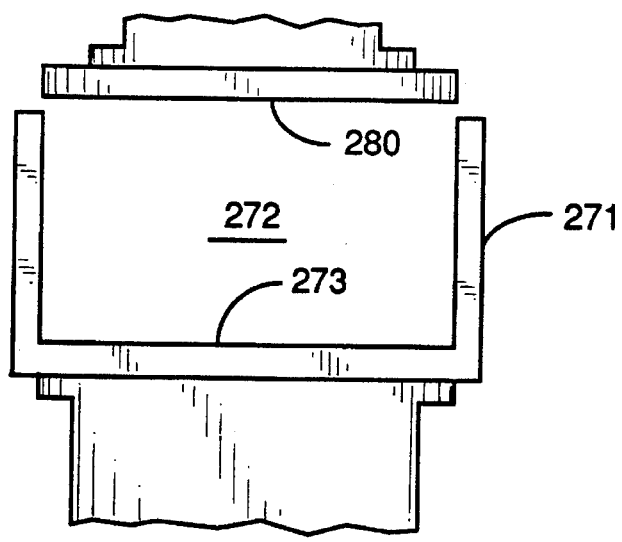
FIGS. 7 and 8, respectively, are cross-sectional illustrations of another embodiment of the present invention wherein local forces normal to the bottom plate may be measured.
Figure 8:
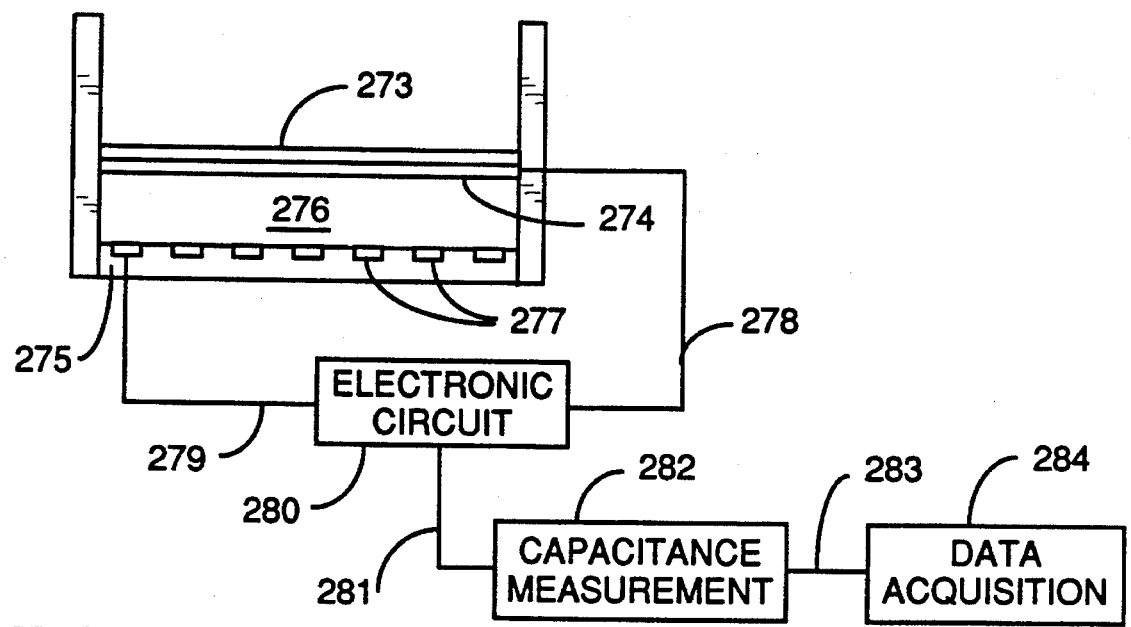

Referring to FIGS. 7 and 8, a further embodiment of the present invention will be considered. This embodiment is suitable for use with materials where the normal forces exhibited by the material under shear are small or where there is a need to measure local forces normal to the plane of shear, such as in the case of biological fluids, polymer solutions, and the like. In this embodiment of the invention, the stationary lower plate 271 is generally cup-shaped and provides an upwardly open chamber 272 which receives the specimen. The overlying rotatable plate 280 is structured to be received within chamber 272.

Figure 9A:
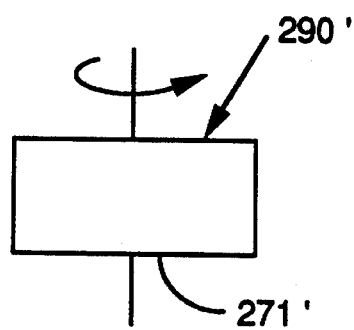
FIGS. 9A and 9B show alternate configurations for the upper rotatable plates.
Figure 9B:
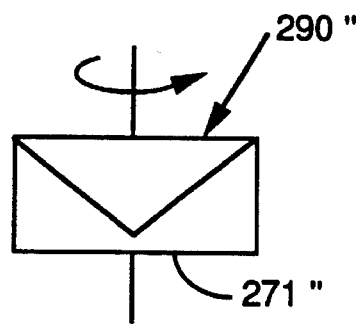

The bottom surface of the lower plate 271 is made out of a flexible membrane 273, the underside of which consists of an electrically conducting membrane 274. FIG. 8 shows the details of the stationary bottom plate 271 which consists of a unique transducer. The flexible membrane 273 is separated from the rigid bottom surface 275 by means of a relatively small fluid gap 276, which may be filled with air or any non-conducting liquid or gas. The rigid bottom surface 275 has embedded in it a plurality of small metallic plates 277 which may be the size of a pin head and which are connected to an electronic circuit 280. The electronic circuit 280 is electrically connected to conductive membrane 274 by lead 278 and to the rigid bottom surface 275 by lead 279. The output signal from electronic circuit is transferred by lead 281 to capacitive measurement unit 282 and which outputs signals over lead 283 to data acquisition unit 284. The embedded metallic plates 277 and the conducting membrane 274 form the two plates of a series of capacitors. In testing a specimen, when a load is applied to the flexible membrane 273, the gap between the conducting membrane and the embedded metallic plates 277 changes which, in turn, changes the capacitance at each of the locations where the embedded metallic plates 277 are located. Knowing the capacitance at each location, one can determine the deflection of the membrane 273 from its initial position and the force required to achieve this deflection. Before the stationary plate 271 is placed in the instrument, it is calibrated using a known load and known gap between the conducting membrane 273 and the embedded metallic plates 277. The top plate can be either a plate 290' or a cone 290", for example, as shown in FIGS. 9A and 9B which are received respectively in lower plates 271'. This transducer is ideal for measuring the forces in small sample volumes as is the case with bio-fluids, such as blood, plasma, polymer solutions, and the like. In addition, knowledge of the local normal forces will greatly enhance the ability to characterize the rheological properties of the samples.

Figure 10:
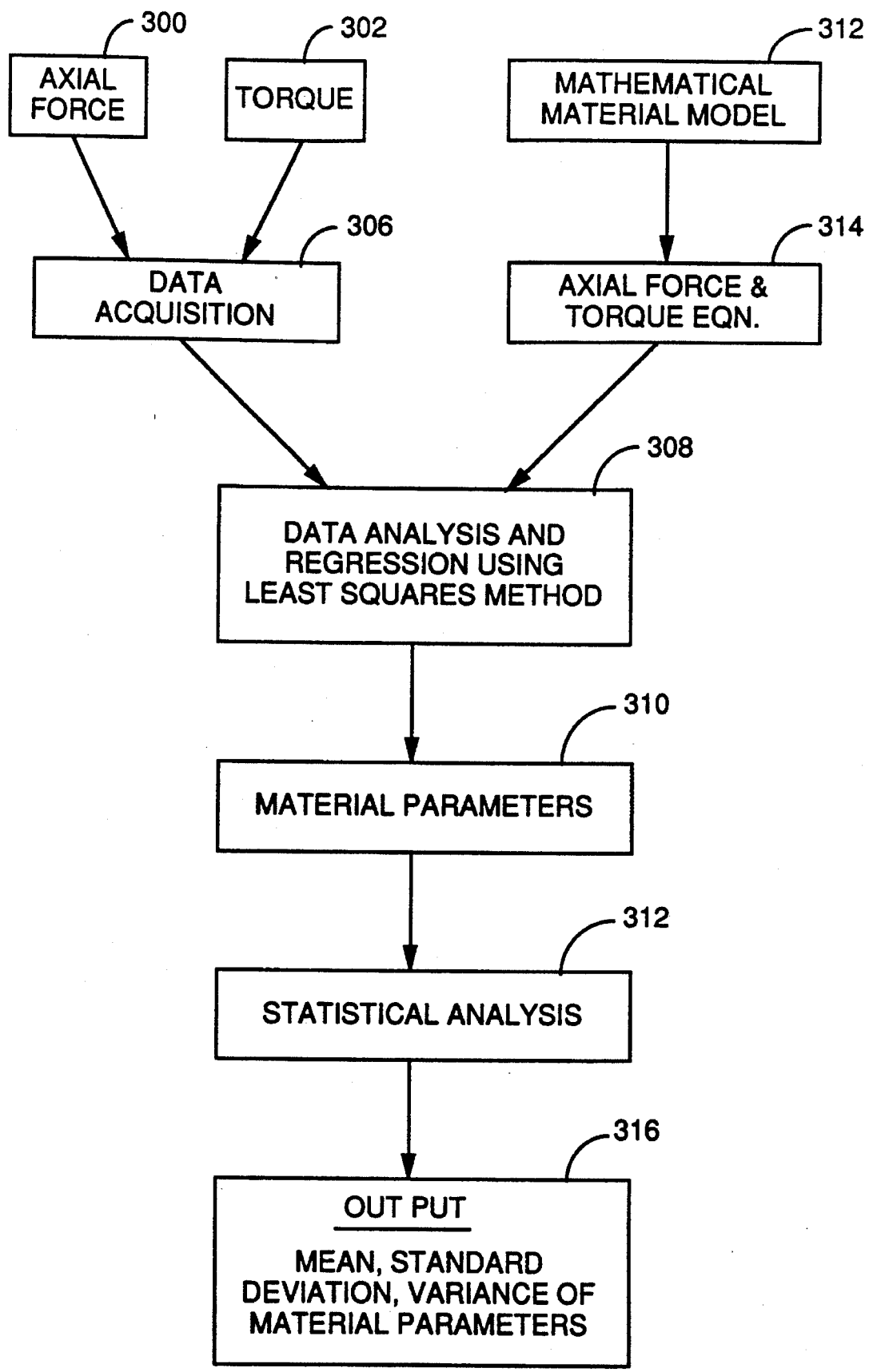
FIG. 10 is a flow diagram of a method of the present invention.

Referring to FIG. 10, a flow chart of the processing of data received within computer means, such as computer 32 in FIG. 1, will be considered. The measured axial force 300 and torque 302 pass through data acquisition unit 306 and to computer 308. Also introduced into the computer 308 is the mathematical material model 312 which is processed by the axial force and torque equation 314 with the output going to computer 308. The computer 308 processes the actual measured data on the axial force and torque and the mathematical material model employing data analysis and regression employing the least squares method. The output of the computer 308 provides the material parameters 310 and statistical analysis 312. The final output 316 provides the mean, standard deviation, and variance of the material parameters based on a comparison of the actual data entering computer 308 from data acquisition unit 306 with the mathematical model predictions of axial force and torque supplied to computer 308 by axial force and torque equation unit 314.

It will be appreciated, therefore, that the present invention provides an effective means for enhancing the efficiency of rotary rheometers in working with a wide variety of specimen materials. In one embodiment, this is accomplished by providing "roughened surfaces" on at least one of the two plates and, preferably, on both with the degree of roughness being adjusted according to the nature of the material being processed. All of this is accomplished in a manner which is readily adaptable to existing rotatable rheometers merely by changing the nature of the plate. In another embodiment, a deformable capacitive sensor is provided within the base of the stationary plate.

Whereas particular embodiments of the invention have been described herein for purposes of illustration, it will be evident to those skilled in the art that numerous variations of the details may be made without departing from the invention as set forth in the appended claims.

We claim:

1. Torsional rheometer apparatus for determining rheological properties of a specimen comprising a stationary plate, a rotatable plate substantially coaxially mounted with respect to said stationary plate, said stationary plate and said rotatable plate being structured to receive said specimen therebetween, motor means for effecting rotation of said rotatable plate, at least one of said plates having a roughened specimen engaging surface, whereby slippage between said roughened plate surface and said specimen will be resisted, and piezoelectric transducer means operatively associated with said stationary plate for receiving forces resulting from said rotation of said rotatable plate and emitting responsive signals which provide information regarding axial force and torque from which rheological properties of said specimen may be determined.

2. The torsional rheometer of claim 1 including said roughened surfaces having portions of said surface projecting from said surface.

3. The torsional rheometer of claim 2 including each of said plates having a roughened surface for engaging said specimen.

4. The torsional rheometer of claim 3 including control means for controlling said motor means in a first mode which effects rotary motion of said rotatable plate and in a second mode which effects oscillatory motion of said rotatable plate.

5. The torsional rheometer of claim 3 including said projecting portions of said roughened surface on said stationary plate and said projecting portions of said roughened surface on said rotary plate being of generally the same configuration.

6. The torsional rheometer of claim 5 including said stationary plate being generally cup-shaped and having an upwardly open chamber for receiving said specimen, and said rotatable plate having a diameter less than the diameter of said chamber to permit entry of said rotatable plate into said chamber.

7. The torsional rheometer of claim 3 including said roughened surfaces on said plates being integrally formed.

8. The torsional rheometer of claim 7 including said rheometer being structured to analyze granular material by having projecting elements defining said roughened surface of generally the same size and shape as the average size and shape of said granular material.

9. The torsional rheometer of claim 3 including said roughened surfaces on said plates being provided by coatings.

10. The torsional rheometer of claim 1 including said roughened specimen engaging surface having means for causing an axial component of the shear force created between said plates by the specimen to apply a force to said transducer.

11. The torsional rheometer of claim 10 including said transducer also receiving forces corresponding to the torque created between said plates.

12. Torsional rheometer apparatus for determining rheological properties of a specimen comprising a stationary plate, a rotatable plate substantially coaxially mounted with respect to said stationary plate, said stationary plate and said rotatable plate being structured to receive said specimen therebetween, motor means for effecting rotation of said rotatable plate, at least one of said plates having a roughened specimen engaging surface, whereby slippage between said roughened plate surface and said specimen will be resisted, each said roughened surface having portions of said surface projecting from said surface, each of said plates having a roughened surface for engaging said specimen, and said roughened surfaces being provided by pores in said surfaces.

13. The torsional rheometer of claim 12 including said rheometer being structured to analyze specimens which are gas-solid mixtures with the size of said pores being smaller than the average size of said particles in said specimen, whereby said pores will resist passage of said solids therethrough while permitting air to pass therethrough.

14. The torsional rheometer of claim 13 including said stationary plate and said rotary plate each having air receiving chambers on the opposite side thereof from the specimen engaging surface, and means for injecting air into a first of said chambers for passage through the plate associated therewith through said specimen and into the second said chamber, whereby said specimen will be maintained as a gas-solid mixture.

15. The torsional rheometer of claim 14 including said first chamber being the chamber associated with said stationary plate.

16. A method of determining the rheological properties of a specimen comprising providing a stationary plate and a generally axially aligned rotatable plate, motor means to rotate said rotatable plate, piezoelectric transducer means operatively associated with said stationary plate and computer means operatively associated with said transducer means, introducing said specimen between said plates, employing a roughened surface contacting said specimen on at least one said plate, effecting rotation of said rotatable plate, applying forces resulting from said rotation to said transducer means through said stationary plate, emitting output signals from said transducer means responsive to the torque and axial forces applied to said stationary plate, and determining said rheological properties by introducing said transducer means output signals into said computer means and processing the same therein.

17. The method of determining the rheological properties of a specimen of claim 16 including employing as said roughened surfaces, surfaces having portions projecting therefrom.

18. The method of determining the rheological properties of a specimen of claim 17 including employing roughened surfaces on both said stationary plate and said rotatable plate facing said specimen.

19. The method of determining the rheological properties of a specimen of claim 17 including controlling said motor means in a first mode which effects the rotary motion of said rotatable plate or in a second mode which effects oscillatory motion of said rotatable plate.

20. The method of determining the rheological properties of a specimen of claim 19 including employing as said roughened surfaces on both said stationary plate and said rotary plate roughened surfaces which are generally of the same configuration.

21. The method of determining the rheological properties of a specimen of claim 19 including rotating said rotatable plates repeatedly in 360° degree cycles in the same direction of rotation, and said roughened surface providing an axial component of the shear force created between the plates by the specimen to said transducer means and said transducer means emitting responsive signals.

22. The method of determining the rheological properties of a specimen of claim 19 including oscillating said rotatable plate through an angular arc substantially less than 360° degrees.

23. The method of determining the rheological properties of a specimen of claim 17 including employing as said stationary plate a generally cup-shaped plate having an upwardly open chamber for receiving said specimen, and employing as said rotatable plate a plate having a diameter less than the diameter of said chamber which plate is positioned within said chamber during operation of said rheometer.

24. The method of determining the rheological properties of a specimen of claim 23 including employing as said roughened surfaces a coating on the surface of said plates.

25. The method of determining the rheological properties of a specimen of claim 17 including employing as said roughened surfaces roughened surfaces integrally formed on said plates.

26. The method of determining the rheological properties of a specimen of claim 17 including using said rheological method in analyzing granular material, and employing roughened surfaces which have projections generally of the same size and shape as the average size and shape of said granular materials.

27. The method of determining the rheological properties of a specimen comprising providing a stationary plate and a generally axially aligned rotatable plate, motor means to rotate said rotatable plate, transducer means operatively associated with said stationary plate and computer means operatively associated with said transducer means, introducing said specimen between said plates, employing a roughened surface contacting said specimen on at least one said plate, effecting rotation of said rotatable plate, emitting output signals from said transducer means responsive to forces applied to said stationary plate, and determining said rheological properties by introducing said output signals into said computer means and processing the same therein, and employing as said roughened surfaces pores in said surfaces.

28. The method of determining the rheological properties of a specimen of claim 27 including using said process to analyze gas-solid specimens which are gas-solid mixtures, employing pores of a size no larger than the size of a major portion of the particles in said specimen, and establishing air flow through said specimen during testing.

29. The method of determining the rheological properties of a specimen of claim 27 including providing air receiving chambers behind each of said plates in communication with the specimen through the pores in said plate, and injecting air into the chamber associated with said stationary plate and causing said air to flow through said specimen through the pores in said rotatable plate and into a chamber operatively associated with said rotatable plate.

30. The method of determining the rheological properties of a specimen of claim 29 including said stationary plate chamber underlying said rotatable plate chamber.

31. A method of determining rheological properties of a specimen comprising providing a stationary plate and a generally axially aligned rotatable plate, means for axially rotating said rotatable plate, piezoelectric transducer means operatively associated with said stationary plate and computer means operatively associated with said transducer means, introducing said specimen between said plates, effecting rotation of said rotatable plate, applying forces resulting from said rotation to said transducer means and said computer means employing responsive output from said transducer means to determine axial force and torque, and employing said axial force and torque to determine rheological properties of said specimen by said computer means.

32. The method of claim 31 including employing computer means to effect said rheological property determination.

33. The method of claim 32 including within said computer means comparing said axial force and torque with axial force and torque information obtained from a mathematical material model.

34. The method of claim 39 including mathematically determining the desired axial force and torque, and determining the mean, standard deviation, and variance of the measured axial force and torque from the mathematically determined axial force and torque.

* * * * *